US010350170B2

(12) United States Patent
Yamane et al.

(10) Patent No.: US 10,350,170 B2
(45) Date of Patent: Jul. 16, 2019

(54) SOLID PREPARATION

(71) Applicant: Takeda Pharmaceutical Company Limited, Osaka (JP)

(72) Inventors: Ikuro Yamane, Osaka (JP); Yukihiro Nomura, Osaka (JP); Yutaka Nishimoto, Osaka (JP); Wataru Hoshina, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/553,852

(22) PCT Filed: Feb. 25, 2016

(86) PCT No.: PCT/JP2016/055540
§ 371 (c)(1),
(2) Date: Aug. 25, 2017

(87) PCT Pub. No.: WO2016/136849
PCT Pub. Date: Sep. 1, 2016

(65) Prior Publication Data
US 2018/0036250 A1 Feb. 8, 2018

(30) Foreign Application Priority Data
Feb. 26, 2015 (JP) ................................. 2015-037462

(51) Int. Cl.
| A61K 9/36 | (2006.01) |
| A61K 9/20 | (2006.01) |
| A61K 31/519 | (2006.01) |
| A61K 47/10 | (2017.01) |
| A61K 47/14 | (2017.01) |
| A61K 47/34 | (2017.01) |
| A61K 9/28 | (2006.01) |

(52) U.S. Cl.
CPC .............. *A61K 9/2031* (2013.01); *A61K 9/20* (2013.01); *A61K 9/2018* (2013.01); *A61K 9/2054* (2013.01); *A61K 9/2886* (2013.01); *A61K 31/519* (2013.01); *A61K 47/10* (2013.01); *A61K 47/14* (2013.01); *A61K 47/34* (2013.01)

(58) Field of Classification Search
CPC ....... A61K 9/2866; A61K 9/28; A61K 31/519
USPC .............................. 424/480, 465; 514/260.1
See application file for complete search history.

(56) References Cited

U.S. PATENT DOCUMENTS

| 5,534,534 A | 7/1996 | Makino et al. |
| 5,573,777 A * | 11/1996 | Serpelloni ............ A61K 9/2018 424/440 |
| 7,300,935 B2 | 11/2007 | Cho et al. |
| 8,058,280 B2 | 11/2011 | Cho et al. |
| 8,735,401 B2 | 5/2014 | Cho et al. |
| 9,346,822 B2 | 5/2016 | Cho et al. |
| 9,758,528 B2 | 9/2017 | Fukuoka et al. |
| 10,150,778 B2 | 12/2018 | Miwa |
| 2005/0222174 A1 | 10/2005 | Furuya et al. |
| 2006/0160829 A1 | 7/2006 | Cho et al. |
| 2009/0186890 A1* | 7/2009 | Gellert .................. A61K 9/284 514/234.5 |
| 2011/0172249 A1 | 7/2011 | Kamikawa et al. |
| 2014/0199236 A1 | 7/2014 | Chen et al. |
| 2015/0266891 A1 | 9/2015 | Fukuoka et al. |
| 2017/0210753 A1 | 7/2017 | Fukuoka et al. |
| 2018/0319816 A1 | 11/2018 | Miwa et al. |

FOREIGN PATENT DOCUMENTS

| EP | 2 329 823 A1 | 6/2011 |
| JP | H-08-295693 A | 11/1996 |
| JP | 2001-278884 A | 10/2001 |
| JP | 2003-292492 A | 10/2003 |
| JP | 2004-250439 A | 9/2004 |
| WO | WO-95/28405 A1 | 10/1995 |
| WO | WO-00/56739 A1 | 9/2000 |
| WO | WO-2004/067535 A1 | 8/2004 |
| WO | WO-2010/026993 A1 | 3/2010 |

OTHER PUBLICATIONS

Miwa et al. "Discovery of 1-{4-[1-(2,6-difluorobenzyl)-5-[(dimethylamino)methyl]-3-(6-methoxypyridazin-3-yl)-2,4-dioxo-1,2,3,4-tetrahydrothieno[2,3-d]pyrimidin-6-yl]phenyl}-3-methoxyurea as . . . " J. Med. Chem. 2011, Vo. 54, pp. 4998-5012.*
International Search Report dated May 31, 2016, for PCT Application No. PCT/JP2016/055540, filed on Feb. 25, 2016, 9 pages (English translation included herewith).
Written Opinion of the International Searching Authority dated May 31, 2016, for PCT Application No. PCT/JP2016/055540, filed on Feb. 25, 2016, 13 pages (English translation included herewith).
Replacement Extended European Search Report dated Nov. 12, 2018, for EP Application No. 16 755 593.7, filed on Feb. 25, 2016, 9 pages.

* cited by examiner

*Primary Examiner* — Shengjun Wang
(74) *Attorney, Agent, or Firm* — Cooley LLP

(57) ABSTRACT

Provided is a solid preparation showing improved stability of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea and a salt thereof in the solid preparation, and a method of stabilizing the compound in a solid preparation.
A tablet containing not less than 25 mass % of the compound; a solid preparation containing (1) the compound, and (2) a fat and oil-like substance having a low melting point, which is selected from polyethylene glycol, glycerol monostearate and triethyl citrate; a method of stabilizing the compound in a tablet, including adding not less than 25 mass % of the compound; and a method of stabilizing the compound, including adding a fat and oil-like substance having a low melting point, which is selected from polyethylene glycol, glycerol monostearate and triethyl citrate to a solid preparation containing the compound.

14 Claims, No Drawings

SOLID PREPARATION

CROSS-REFERENCE TO RELATED APPLICATIONS

This application is a U.S. National Stage Application under 35 U.S.C. § 371 of International Application No. PCT/JP2016/055540, filed on Feb. 25, 2016, which claims priority to Japanese Application No. 2015/037462, filed on Feb. 26, 2015, the subject matter of each of which are herein incorporated by reference in their entirety.

TECHNICAL FIELD

The present invention relates to a solid preparation (e.g., tablet) showing improved stability of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea (to be also referred to as compound A in the present specification) and a salt thereof in the solid preparation, and a method of stabilizing compound A and a salt thereof in a solid preparation.

BACKGROUND ART

Patent document 1 discloses that a compound represented by a formula and a salt thereof, encompassing compound A and a salt thereof, have a superior gonadotropic hormone-releasing hormone antagonistic action and can be used, for example, as a prophylactic or therapeutic agent for hormone dependent diseases, together with the production method of the compound.

Patent document 2 discloses a preparation containing a compound represented by the above-mentioned formula and a salt thereof, which characteristically contains an organic acid and shows improved oral absorbability.

DOCUMENT LIST

Patent Documents

[patent document 1] WO 2004/067535
[patent document 2] WO 2010/026993

SUMMARY OF THE INVENTION

Problems to be Solved by the Invention

While compound A and a salt thereof are stable to temperature, humidity and the like when they are alone and in a solid state, the present inventors have found a problem that a decomposed product of compound A or a salt thereof increases chronologically when compound A or a salt thereof is formulated as a solid preparation (e.g., tablet) according to a preparation formulation containing other components.

The present invention aims to solve such newly-found problem, and the present invention aims to provide a solid preparation (e.g., tablet) showing improved stability of compound A and a salt thereof in the solid preparation, and a method of stabilizing compound A and a salt thereof in a solid preparation.

Means of Solving the Problems

As a result of intensive studies conducted in an attempt to solve the aforementioned problems, the present inventors have found that chronological decomposition of compound A and a salt thereof in a tablet is suppressed by setting the content of compound A and a salt thereof in the tablet to not less than 25 mass %; in other words, that compound A and a salt thereof in a tablet are stabilized.

In addition, as a result of intensive studies conducted in an attempt to solve the aforementioned problems, the present inventors have found that chronological decomposition of compound A and a salt thereof in a solid preparation is suppressed by adding a fat and oil-like substance having a low melting point, which is selected from polyethylene glycol, glycerol monostearate and triethyl citrate, to a solid preparation (e.g., tablet); in other words, that compound A and a salt thereof in a solid preparation are stabilized.

Based on the above-mentioned finding, the present inventors have further conducted intensive studies and completed the present invention.

That is, the present invention provides the following.

[1] A tablet comprising not less than 25 mass % of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof.

[2] The tablet of the above-mentioned [1], comprising D-mannitol particles having an average particle size of 60-500 μm.

[3] The tablet of the above-mentioned [1], comprising D-mannitol particles having an average particle size of 60-250 μm.

[4] A method of stabilizing N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof in a tablet, comprising adding not less than 25 mass % of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof.

[5] The method of the above-mentioned [4], further comprising adding D-mannitol particles having an average particle size of 60-500 μm.

[6] The method of the above-mentioned [4], further comprising adding D-mannitol particles having an average particle size of 60-250 μm.

[7] A solid preparation comprising
(1)  N-(4-(1-(2,6-difluorobenzyl)-5-((dimethylamino) methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof and
(2) a fat and oil-like substance having a low melting point, which is selected from polyethylene glycol, glycerol monostearate and triethyl citrate.

[8] The solid preparation of the above-mentioned [7], wherein the fat and oil-like substance having a low melting point is polyethylene glycol.

[9] The solid preparation of the above-mentioned [7], wherein the fat and oil-like substance having a low melting point is polyethylene glycol having an average molecular weight of about 6000 to about 120000.

[10] A method of stabilizing N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof, comprising adding a fat and oil-like substance having a low melting point, which is selected from polyethylene glycol, glycerol monostearate and triethyl citrate to a solid preparation comprising N-(4-(1-(2,6-difluorobenzyl)-5-((dimethylamino)methyl)-3-(6- methoxy-3-pyridazinyl)-2,4-dioxo-1,2,3,4-tetrahydrothieno [2,3-d]pyrimidin-6-yl)phenyl)-N'-methoxyurea or a salt thereof.

[11] The method of the above-mentioned [10], wherein the fat and oil-like substance having a low melting point is polyethylene glycol.

[12] The method of the above-mentioned [10], wherein the fat and oil-like substance having a low melting point is polyethylene glycol having an average molecular weight of about 6000 to about 120000.

Effect of the Invention

According to the present invention, a solid preparation (e.g., tablet) showing improved stability of compound A and a salt thereof in the solid preparation, and a method of stabilizing compound A and a salt thereof in a solid preparation can be provided.

DETAILED DESCRIPTION OF THE INVENTION

The present invention is explained in detail below.

As a salt of compound A, a physiologically acceptable acid addition salt is preferable. As such salt, salt with inorganic acid (e.g., hydrochloric acid, hydrobromic acid, nitric acid, sulfuric acid, phosphoric acid), salt with organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid) and the like are used.

1. Tablet Containing Compound A or a Salt Thereof at a High Content

In one embodiment, the present invention relates to a tablet containing compound A or a salt thereof at a high content, specifically, a tablet containing compound A or a salt thereof at not less than 25 mass % (preferably not less than 35 mass %, more preferably not less than 40 mass %) (hereinafter sometimes to be abbreviated as the tablet of the present invention).

In the tablet of the present invention, the content of compound A or a salt thereof is, for example, not more than 80 mass % (preferably not more than 75 mass %).

Since the tablet of the present invention contains not less than 25 mass % (preferably not less than 35 mass %, more preferably not less than 40 mass %) of compound A or a salt thereof, it can improve the stability of compound A and a salt thereof in the tablet as compared to a tablet containing compound A or a salt thereof at a low content (e.g., less than 25 mass %). In addition, since the tablet of the present invention contains compound A or a salt thereof at a high content, the tablet can be downsized, which in turn is expected to provide an improving effect on the dosing compliance of the patients.

The present inventors have found that a tablet containing compound A or a salt thereof at a high content (preferably not less than 25 mass %, preferably not less than 30 mass %, more preferably not less than 35 mass %, further preferably not less than 40 mass %) can be obtained by adding D-mannitol particles having an average particle size of 60-500 μm (more preferably 60-250 μm, further preferably 70-200 μm, particularly preferably 80-150 μm) as an excipient to the tablet containing compound A or a salt thereof. In the present specification, the average particle size refers to a value generally called a median diameter, which corresponds to 50% of the cumulative distribution (volume distribution) of powder particles. The average particle size can be measured by a particle laser diffraction particle size analyzer (HELOS system and RODOS dispersing unit, Sympatech) at a dispersing pressure of 2.0 bar.

D-mannitol particles having an average particle size within the above-mentioned range can be produced by a method known per se, and is not particularly limited. For example, it can be produced by a spray dry production method. As a D-mannitol particles having an average particle size within the above-mentioned range, a commercially available product (e.g., PEARLITOL 100SD, PEARLITOL 200SD, PEARLITOL 300DC, PEARLITOL 400DC, all by ROQUETTE) can also be used. As the above-mentioned D-mannitol particles, D-mannitol particles having an average particle size of 75-150 μm (e.g., PEARLITOL 100SD) are preferable.

In the tablet of the present invention, the content of D-mannitol particles is preferably 10-75 mass %, more preferably 12-70 mass %, further preferably 15-65 mass %, further more preferably 15-60 mass %.

The tablet of the present invention may further contain additives conventionally used in the pharmaceutical field. Examples of the additive include excipient, binder, disintegrant, lubricant, colorant, pH adjuster, surfactant, sweetener, flavor, coating base, and coating additive. Unless particularly indicated, these additives are used in amounts conventionally employed in the pharmaceutical field.

Examples of the excipient include mannitol (e.g., D-mannitol {e.g., PEARLITOL 50C (trade name); ROQUETTE}); crystalline cellulose; starches such as corn starch, potato starch, wheat starch, rice starch, partly pregelatinized starch, pregelatinized starch, porous starch and the like; anhydrous calcium phosphate; precipitated calcium carbonate; and calcium silicate, with preference given to D-mannitol and crystalline cellulose.

In the tablet of the present invention, the content of the excipient is preferably 10-75 mass %, more preferably 20-65 mass %.

As the excipient in the present invention, D-mannitol particle or mannitol (e.g., D-mannitol) is preferable, and D-mannitol particle is more preferable. D-mannitol and D-mannitol particle may be used alone or in combination.

When the aforementioned D-mannitol particles are used as an excipient in the present invention, the total amount of the excipient only needs to fall within the above-mentioned range.

When the aforementioned mannitol is used as the excipient in the present invention, the total amount of the excipient is preferably 10-75 mass %, more preferably 12-70 mass %, further preferably 15-65 mass %, further more preferably 15-60 mass %.

Examples of the binder include crystalline cellulose [e.g., crystalline cellulose {e.g., CEOLUS KG-802 (grade: KG-802) (trade name); CEOLUS PH-302 (grade: PH-302) (trade name); Asahi Kasei Chemicals Corporation}, crystalline cellulose (particles), crystalline cellulose (fine particles)], hydroxypropylcellulose [e.g., grade: L, SL, SSL (trade name); Nippon Soda Co., Ltd.], hydroxypropylmethylcellulose [e.g., hypromellose 2910, TC-5 (grade: MW, E, EW, R, RW) (trade name); Shin-Etsu Chemical Co., Ltd.], povidone (polyvinylpyrrolidone), and copolyvidone, with preference given to hydroxypropylcellulose.

In the tablet of the present invention, the content of the binder is preferably 0.5-20 mass %, more preferably 1-10 mass %.

Examples of the disintegrant include corn starch, carboxymethylcellulose, calcium carboxymethylcellulose, sodium carboxymethyl starch, croscarmellose sodium (e.g., Ac-Di-Sol), crospovidone, low-substituted hydroxypropylcellulose (L-HPC), hydroxypropylstarch, sodium starch glycolate, and magnesium alumino metasilicate, with preference given to croscarmellose sodium and sodium starch glycolate.

In the tablet of the present invention, the content of the disintegrant is preferably 1-20 mass %, more preferably 2-10 mass %.

Examples of the lubricant include magnesium stearate, calcium stearate, talc, sucrose esters of fatty acids, and sodium stearyl fumarate, with preference given to magnesium stearate.

In the tablet of the present invention, the content of the lubricant is preferably 0.1-5 mass %, more preferably 0.2-3 mass %.

Examples of the colorant include food colors such as Food Color Yellow No. 5, Food Color Red No. 2, Food Color Blue No. 2 and the like, food lake colors, red ferric oxide, and yellow ferric oxide.

Examples of the pH adjuster include citric acid or a salt thereof, phosphoric acid or a salt thereof, carbonic acid or a salt thereof, tartaric acid or a salt thereof, fumaric acid or a salt thereof, acetic acid or a salt thereof, and amino acid or a salt thereof.

Examples of the surfactant include sodium lauryl sulfate, polysorbate 80, and polyoxyethylene(160)polyoxypropylene(30)glycol.

Examples of the sweetener include aspartame (trade name), acesulfame potassium, sucralose, thaumatin, saccharin sodium, and dipotassium glycyrrhizinate.

Examples of the flavor include menthol, peppermint oil, lemon oil, and vanillin.

Examples of the coating base include sugar coating base, water-soluble film coating base, enteric film coating base, and sustained-release film coating base.

Examples of the sugar coating base include sucrose, and one or more kinds selected from talc, precipitated calcium carbonate, gelatin, gum arabic, pullulan, carnauba wax and the like may be used in combination.

Examples of the water-soluble film coating base include cellulose polymers such as hydroxypropylcellulose [e.g., grade: L, SL, SL-T, SSL (trade name); Nippon Soda Co., Ltd.], hydroxypropylmethylcellulose [e.g., hypromellose 2910, TC-5 (grade: MW, E, EW, R, RW) (trade name); Shin-Etsu Chemical Co., Ltd.], hydroxyethylcellulose, methylhydroxyethylcellulose and the like; synthetic polymers such as polyvinyl acetaldiethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally occurring substances such as shellac and the like.

Examples of the sustained-release film coating base include cellulose polymers such as ethylcellulose and the like; acrylic acid polymers such as aminoalkylmethacrylate copolymer RS [Eudragit RS (trade name)], ethyl acrylate-methyl methacrylate copolymer suspension [Eudragit NE (trade name)] and the like.

Examples of the coating additive include light shielding agents such as titanium oxide and the like; fluidizers such as talc and the like; colorants such as red ferric oxide, yellow ferric oxide and the like; plasticizers such as polyethylene glycol (e.g., macrogol 6000), triethyl citrate, castor oil, polysorbates and the like; organic acids such as citric acid, tartaric acid, malic acid, ascorbic acid and the like.

Two or more kinds of the above-mentioned additives may be used as a mixture at an appropriate ratio.

The tablet of the present invention may be film coated for the purpose of improving easy administrability, hardness and the like. Examples of the coating base and coating additive to be used for the film coating include those similar to the ones used for the aforementioned additive.

When the tablet of the present invention is film-coated, the film coating layer is formed in a proportion of generally 1-10 parts by mass, preferably 2-6 parts by mass, per 100 parts by mass of the tablet.

When the tablet of the present invention a film-coated tablet, the contents of compound A or a salt thereof and an additive in a core tablet before applying film coating are preferably within the aforementioned ranges.

The tablet of the present invention is preferably a tablet containing compound A or a salt thereof, an excipient (e.g., D-mannitol particles, D-mannitol, preferably D-mannitol particles), a disintegrant (e.g., sodium starch glycolate), a binder (e.g., hydroxypropylcellulose), and a lubricant (e.g., magnesium stearate), wherein the content of compound A or a salt thereof is not less than 25 mass % (preferably not less than 30 mass %, more preferably not less than 35 mass %, further preferably not less than 40 mass %).

In addition, the tablet of the present invention is preferably a film-coated tablet wherein a tablet (core tablet) containing compound A or a salt thereof, an excipient (e.g., D-mannitol particles), a disintegrant (e.g., sodium starch glycolate), a binder (e.g., hydroxypropylcellulose), and a lubricant (e.g., magnesium stearate) is coated with a coating base (e.g., hydroxypropylmethylcellulose) and a coating additive (e.g., titanium oxide, red ferric oxide), and the content of compound A or a salt thereof is not less than 25 mass % (preferably not less than 30 mass %, more preferably not less than 35 mass %, further preferably not less than 40 mass %) relative to the core tablet.

The tablet of the present invention preferably further contains a fat and oil-like substance having a low melting point, which is selected from polyethylene glycol, glycerol monostearate and triethyl citrate. When a fat and oil-like substance having a low melting point is added to the tablet of the present invention, the content etc. thereof are the same as those described below in "2. Solid preparation containing compound A or a salt thereof and a fat and oil-like substance having a low melting point".

The tablet of the present invention is produced by appropriately combining operations such as granulation, mixing, tableting (compression molding), coating and the like.

Granulation is performed using, for example, a granulation machine such as a high shear granulator, a fluid bed granulator, a dry granulator or the like.

Mixing is performed using, for example, a mixer such as a V-type mixer, a tumbler mixer or the like.

Tableting (compression molding) is performed by punching using, for example, a single punch tableting machine or a rotary tableting machine.

Coating is performed using, for example, a film coating apparatus. As the coating base here, those exemplified as the aforementioned additive can be mentioned.

Two or more kinds of the above-mentioned coating base may be used as a mixture at an appropriate ratio. Also, a coating additive may be used during coating.

The tablet of the present invention can be produced, for example, according to the following production steps. Each starting material in the following production steps is used in such amount as to achieve the aforementioned content in the finally obtained tablet.

1) Compound A or a salt thereof, and an excipient (e.g., D-mannitol particles, D-mannitol, crystalline cellulose, preferably D-mannitol particles) are mixed together with other additive (e.g., disintegrant (e.g., sodium starch glycolate)) as necessary, the mixture is granulated while spraying a solution obtained by dissolving or dispersing a binder (e.g., hydroxypropylcellulose) in a solvent or dispersing medium (e.g., water), dried and sieved as necessary to give a granulated powder (or a sieved powder).

2) An additive (e.g., lubricant (e.g., magnesium stearate)) is added to the obtained granulated powder (or sieved powder) as necessary, and they are mixed to give granules for tableting.

3) The granules are tableted to give a core tablet.

4) A film coating solution is sprayed on the obtained core tablet, when desired, to give a film-coated tablet.

The present invention also relates to a stabilizing method of the following compound A or a salt thereof.

One embodiment of the present invention relates to method of stabilizing compound A or a salt thereof in a tablet, comprising adding not less than 25 mass % (preferably not less than 30 mass %, more preferably not less than 40 mass %) of compound A or a salt thereof (hereinafter sometimes to be abbreviated as the method of the present invention).

In the present specification, addition and containing mean the same and, for example, adding not less than 25 mass % of compound A or a salt thereof to a tablet means that the tablet contains not less than 25 mass % of compound A or a salt thereof.

In the method of the present invention, further addition of (1) D-mannitol particles having an average particle size of 60-500 μm (preferably 60-250 μm, more preferably 70-200 μm, particularly preferably 80-150 μm) or (2) D-mannitol having an average particle size of 30-60 μm {e.g., PEARLITOL 50C (trade name); ROQUETTE}) is preferable, and addition of the above-mentioned D-mannitol particles is more preferable. D-mannitol and D-mannitol particles may be used alone or in combination.

The tablet by the method of the present invention is prepared in the same manner as in the aforementioned formulation of the tablet of the present invention. For example, the amount of the D-mannitol particles or D-mannitol is analogous to that in the tablet of the present invention.

The method of the present invention may include a step of confirming the stabilizing effect (e.g., step of measuring the content of a decomposed product (U-2) of compound A or a salt thereof in the tablet etc.). The step of measuring the content of the decomposed product can be performed according to, for example, the below-mentioned Experimental Example 1.

2. Solid Preparation Containing Compound A or a Salt Thereof and a Fat and Oil-Like Substance Having a Low Melting Point Another embodiment of the present invention relates to a solid preparation containing (1) compound A or a salt thereof, and (2) a fat and oil-like substance having a low melting point, which is selected from polyethylene glycol, glycerol monostearate and triethyl citrate (hereinafter sometimes to be abbreviated as the solid preparation of the present invention).

In the solid preparation of the present invention, the content of compound A or a salt thereof is preferably not less than 4 mass % and less than 100 mass %, more preferably 4-80 mass %, further preferably 18-50 mass %.

Since the solid preparation of the present invention contains a fat and oil-like substance having a low melting point, which is selected from polyethylene glycol, glycerol monostearate and triethyl citrate, it can improve the stability of compound A and a salt thereof in the solid preparation. These fat and oil-like substances having a low melting point may be used alone or two or more kinds thereof may be used in combination.

In the solid preparation of the present invention, the content of a fat and oil-like substance having a low melting point, which is selected from polyethylene glycol, glycerol monostearate and triethyl citrate is, for example, 0.1-10 mass %.

While the preferable range of the above-mentioned content varies depending on the kind of the fat and oil-like substance having a low melting point to be added to a solid preparation, for example, when the above-mentioned fat and oil-like substance having a low melting point is polyethylene glycol (e.g., polyethylene glycol 6000), it is, for example, 0.1-4.0 mass % (preferably 0.2-2.0 mass %, more preferably 0.2-1.7 mass %, further preferably 0.2-0.4 mass %). When, for example, the above-mentioned fat and oil-like substance having a low melting point is glycerol monostearate or triethyl citrate, it is 0.1-10 mass % (preferably, 1.0-4.0 mass %).

In the present invention, a fat and oil-like substance having a low melting point is particularly preferably polyethylene glycol.

Examples of the polyethylene glycol include polyethylene glycol having an average molecular weight of 200-7000000 (preferably about 6000-about 120000, more preferably about 8000-about 100000) (e.g., polyethylene glycol 400 (the Japanese Pharmacopoeia), and polyethylene glycol 6000 (the Japanese Pharmacopoeia)), POLYOX WSR N-10 (trade name), POLYOX WSR N-205 (trade name), POLYOX WSR N-12K (trade name), POLYOX WSR 303 (trade name), preferably POLYOX WSR N-10 (trade name), polyethylene glycol 6000, more preferably polyethylene glycol 6000) is preferable. As used herein, polyethylene glycol is a generic term of compounds represented by the formula $H(OCH_2CH_2)_nOH$ wherein n is a natural number (compound wherein n is not less than 2000 is sometimes referred to as polyethylene oxide).

Here, polyethylene glycol 6000 is also referred to as macrogol 6000 in the Japanese Pharmacopoeia (an average molecular weight thereof is generally said to be 7300-9300). In addition, polyethylene glycol 6000 is referred to as polyethylene glycol 8000 in the NATIONAL FORMULARY.

In the present specification, the "average molecular weight" in the explanation of polyethylene glycol means "number average molecular weight".

These fat and oil-like substances having a low melting point, which are in a solid form or a liquid form, are added to an active ingredient (compound A or a salt thereof). The present invention is more advantageously applied to a solid preparation (granule, tablet and the like, preferably tablet) produced by molding (granulation, compression molding and the like).

The solid preparation of the present invention is generally produced by adding the above-mentioned fat and oil-like substance having a low melting point to an active ingredient (compound A or a salt thereof) and molding the mixture.

The addition is performed by an addition method generally used for preparations, for example, mixing, kneading, screening, stirring and the like. For example, a fat and oil-like substance having a low melting point may be directly added to the active ingredient and mixed, and a solvent may be further added and mixed therewith, and the mixture can be kneaded, granulated and dried by conventional methods.

It is also possible to dissolve a fat and oil-like substance having a low melting point in a suitable solvent, mix same with an active ingredient, and knead, granulate and dry same by conventional methods. Furthermore, a solution containing a fat and oil-like substance having a low melting point and a solution containing an active ingredient may be separately sprayed on a powder of excipient and the like.

As the above-mentioned suitable solvent, a solvent that does not adversely influence the active ingredient, for example, water, dimethyl formamide, acetone, ethanol, propyl alcohol, isopropyl alcohol, butyl alcohol, methylene chloride, and trichloroethane are used.

After the completion of addition, a tablet can be produced by a known compression molding means. Compression molding means compressing under pressurization to give a desired form, which most generally refers to, for example, tableting and the like.

The solid preparation of the present invention may further contain an additive conventionally used in the pharmaceutical field. Examples of the additive include excipient, binder, disintegrant, lubricant, colorant, pH adjuster, surfactant, sweetener, flavor, coating base, coating additive and the like. Unless particularly indicated, these additives are used in amounts conventionally employed in the pharmaceutical field.

Examples of these additives include those similar to the additives exemplified for the aforementioned tablet of the present invention.

In the solid preparation of the present invention, the excipient is preferably D-mannitol, D-mannitol particle or crystalline cellulose, more preferably D-mannitol or crystalline cellulose. The content of the excipient is preferably 10-70 mass %, more preferably 16-64 mass %.

In the solid preparation of the present invention, the binder is preferably hydroxypropylcellulose. The content of the binder is preferably 0.5-20 mass %, more preferably 1-10 mass %.

In the solid preparation of the present invention, the disintegrant is preferably croscarmellose sodium. The content of the disintegrant is preferably 1-20 mass %, more preferably 2-10 mass %.

In the solid preparation of the present invention, the lubricant is preferably magnesium stearate. The content of the lubricant is preferably 0.1-3 mass %, more preferably 0.2-2 mass %.

The solid preparation of the present invention may be film coated for the purpose of improving easy administrability, hardness and the like. Examples of the coating base and coating additive to be used for the film coating include those exemplified as the aforementioned additive.

When the solid preparation of the present invention is film-coated, the film coating layer is formed in a proportion of generally 1-10 parts by mass, preferably 2-6 parts by mass, per 100 parts by mass of the solid preparation.

When the solid preparation of the present invention is a film-coated tablet, the contents of compound A or a salt thereof, a fat and oil-like substance having a low melting point and an additive in the core tablet before application of film coating are preferably within the aforementioned ranges.

The solid preparation of the present invention is preferably a tablet containing compound A or a salt thereof; a fat and oil-like substance having a low melting point, which is selected from polyethylene glycol, glycerol monostearate and triethyl citrate; excipient (e.g., D-mannitol, crystalline cellulose); a disintegrant (e.g., croscarmellose sodium); a binder (e.g., hydroxypropylcellulose); and a lubricant (e.g., magnesium stearate).

The solid preparation of the present invention is preferably a film-coated tablet wherein a tablet (core tablet) containing compound A or a salt thereof; a fat and oil-like substance having a low melting point, which is selected from polyethylene glycol, glycerol monostearate and triethyl citrate; an excipient (e.g., D-mannitol, crystalline cellulose); a disintegrant (e.g., croscarmellose sodium); a binder (e.g., hydroxypropylcellulose); and a lubricant (e.g., magnesium stearate) is coated with a coating base (e.g., hydroxypropylmethylcellulose) and a coating additive (e.g., titanium oxide, red ferric oxide, yellow ferric oxide).

The solid preparation of the present invention is produced by appropriately combining operations such as granulation, mixing, tableting (compression molding), coating and the like. Granulation, mixing, tableting (compression molding) and coating can be performed according to the method and steps exemplified for the aforementioned tablet of the present invention.

The solid preparation of the present invention can be produced, for example, according to the following production steps. Each starting material in the following production steps is used in such amount as to achieve the aforementioned content in the finally obtained solid preparation.

1) Compound A or a salt thereof, and an excipient (e.g., D-mannitol, crystalline cellulose) are mixed together with other additives as necessary, the mixture is granulated while spraying a solution obtained by dissolving or dispersing a binder (e.g., hydroxypropylcellulose) and a fat and oil-like substance having a low melting point, which is selected from polyethylene glycol, glycerol monostearate and triethyl citrate, in a solvent or dispersing medium (e.g., water), dried and sieved as necessary to give a granulated powder (or a sieved powder).

2) An additive (e.g., lubricant (e.g., magnesium stearate), disintegrant (e.g., croscarmellose sodium)) is added to the obtained granulated powder (or sieved powder) as necessary, and the mixture is mixed to give granules for tableting.

3) The granules are tableted to give a core tablet.

4) A film coating solution is sprayed on the obtained core tablet, when desired, to give a film-coated tablet.

The aforementioned tablet of the present invention and the solid preparation of the present invention (hereinafter these are collectively referred to the solid preparation of the present invention) have low toxicity and can be safely administered orally to mammals (e.g., mouse, rat, rabbit, cat, dog, bovine, horse, monkey, human).

The solid preparation of the present invention is, for example, useful for the prophylaxis or treatment of hormone-dependent diseases (e.g., prostate cancer) and the like.

The dose of the solid preparation of the present invention varies depending on the severity of symptoms; age, sex, body weight and sensitivity of the administration subject; and timing, frequency and the like of administration, and is not particularly limited as long as the object of the present invention is achieved. For example, when it is used as an oral preparation for the treatment of the aforementioned hormone dependency diseases (e.g., prostate cancer), about 0.01-30 mg, preferably about 0.02-10 mg, more preferably 0.1-10 mg, most preferably 0.5-10 mg, per 1 kg body weight based on a free form of compound A, can be administered to a mammal (e.g., human) in 1 to 4 portions per day.

The solid preparation of the present invention is preferably a tablet and the size thereof varies depending on the shape of the tablet (e.g., round, caplet, oblong etc.). It only needs to be a size that can be easily taken by the patients.

As the solid preparation of the present invention, a tablet containing 40-120 mg, preferably 80 mg or 120 mg, of compound A or a salt thereof based on compound A (free form) per tablet can be mentioned.

In the solid preparation of the present invention, compound A or a salt thereof can also be used in combination with one or more different kinds of medicaments.

In addition, the solid preparation of the present invention preferably contains D-mannitol particles as an excipient. The content etc. of the D-mannitol particles in the solid preparation of the present invention are the same as those detailedly described in "1. Tablet containing compound A or a salt thereof at a high content".

Another embodiment of the present invention relates to a method of stabilizing compound A or a salt thereof, comprising adding a fat and oil-like substance having a low melting point, which is selected from polyethylene glycol, glycerol monostearate and triethyl citrate to a solid preparation containing compound A or a salt thereof.

The order of addition of each component is not particularly limited, and, for example, as mentioned above, a fat and oil-like substance having a low melting point may be directly added to an active ingredient (compound A or a salt thereof) and mixed, and a solvent may be further added and mixed therewith, and the mixture can be kneaded, granulated and dried by conventional methods; a fat and oil-like substance having a low melting point may be dissolved in a suitable solvent, uniformly mixed with an active ingredient, and kneaded, granulated and dried by conventional methods; or a solution containing a fat and oil-like substance having a low melting point and a solution containing an active ingredient may be separately sprayed on a powder of excipient and the like. After the completion of addition, a tablet can be produced by a known compression molding means.

Specifically, for example, when the solid preparation is a tablet, compound A or a salt thereof is granulated while spraying a solution obtained by dissolving or dispersing a fat and oil-like substance having a low melting point in a solvent or dispersion medium (e.g., water), and dried to give a granulated powder, and the obtained granulated powder is punched to give a tablet.

The solid preparation by the method is prepared in the same manner as in the aforementioned formulation of the solid preparation of the present invention. For example, the amounts of the fat and oil-like substance having a low melting point, which is selected from polyethylene glycol, glycerol monostearate and triethyl citrate are analogous to those in the solid preparation of the present invention.

This method may include a step of confirming a stabilizing effect (e.g., step of measuring the content of decomposed product (U-2) of compound A or a salt thereof in the solid preparation etc.). The step of measuring the content of the decomposed product can be performed, for example, according to the below-mentioned Experimental Example 1.

EXAMPLES

The present invention is explained in more detail in the following by referring to Examples, Comparative Examples, Reference Examples, and Experimental Examples, which are not to be construed as limitative.

D-mannitol (PEARLITOL 50C (trade name), manufactured by ROQUETTE), D-mannitol particles (PEARLITOL 100SD (trade name), PEARLITOL 200SD (trade name), PEARLITOL 300DC (trade name) or PEARLITOL 400DC (trade name), all manufactured by ROQUETTE), crystalline cellulose (CEOLUS PH-101 or KG-802 (trade name), manufactured by Asahi Kasei Chemicals Corporation), hydroxypropylcellulose (HPC-L (trade name), manufactured by NIPPON SODA CO., LTD.), croscarmellose sodium (Ac-Di-Sol (trade name) manufactured by FMC), sodium starch glycolate (Primojel (trade name), manufactured by DMV), magnesium stearate (Magnesium Stearate (trade name), manufactured by Taihei Chemical Industrial Co., Ltd.), polysorbate 80 (POLYSORBATE 80 (trade name), manufactured by Sanyo Chemical Industries, Ltd.), hydroxypropylmethylcellulose 2910 (TC-5 (trade name), manufactured by Shin-Etsu Chemical Co., Ltd.) (hereinafter sometimes to be abbreviated as hypromellose), polyethylene glycol 6000 (MACROGOL 6000 (trade name), manufactured by Sanyo Chemical Industries, Ltd.), titanium oxide (titanium oxide (trade name) manufactured by Freund Corporation), glycerol monostearate (manufactured by RIKEN VITAMIN CO., LTD.) (sometimes referred to as GMS in the present specification) were the Japanese Pharmacopoeia, 15th Edition, compatible products, red ferric oxide (red ferric oxide (trade name) manufactured by LCW), and triethyl citrate (CITROFLEX 2 (trade name), manufactured by CBC) were Japanese Pharmaceutical Excipients 2003 compatible products, magnesium alumino metasilicate (Neusilin FL2 (trade name), manufactured by Fuji Chemical Industries Co., Ltd.) was the Japanese Pharmaceutical Codex 2002 compatible product, polyethylene glycol 400 (Polyethylene Glycol 400 (trade name), manufactured by Wako Pure Chemical Industries, Ltd.) was a reagent grade product, POLYOX (POLYOX WSR N-10 (trade name), POLYOX WSR N-205 (trade name), POLYOX WSR N-12K (trade name), POLYOX WSR 303 (trade name), all manufactured by Dow Chemical) was the National Formulary compatible product, all of which were used in the following Examples, Comparative Examples, Reference Examples, and Experimental Examples.

Comparative Example 1

A core tablet containing compound A at a composition ratio shown in Table 1-1 was produced as follows.

That is, in a fluid bed granulator/dryer (LAB-1, Powrex Corporation), compound A, D-mannitol, and crystalline cellulose were preheated and mixed, an aqueous solution of hydroxypropylcellulose was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (compact tableting machine, Kikusui Seisakusho Ltd.) with a 6.0 mmφ punch to give core tablets (110 mg per tablet).

The core tablet was placed in a film coating machine (DRC-200, Powrex Corporation), a film coating solution with a composition ratio shown in Table 1-2 was sprayed to give film coated tablets (about 114.0 mg per tablet). The obtained film coated tablets were placed in a glass bottle, which was tightly sealed and preserved at 60° C. for 2 weeks.

TABLE 1-1

| additive | formulation amount (mg/tablet) |
| --- | --- |
| compound A | 5 |
| D-mannitol | 76 |
| crystalline cellulose | 20 |
| hydroxypropylcellulose | 3 |
| croscarmellose sodium | 5 |
| magnesium stearate | 1 |
| Total | 110 |

TABLE 1-2

| additive | formulation amount (mg/tablet) |
| --- | --- |
| hypromellose | 3.56 |
| titanium oxide | 0.40 |
| red ferric oxide | 0.04 |
| Total | 4.00 |

Comparative Example 2

A core tablet containing compound A at a composition ratio shown in Table 2-1 was produced as follows.

That is, in a fluid bed granulator/dryer (FD-5S, Powrex Corporation), compound A, D-mannitol, and crystalline cellulose were preheated and mixed, an aqueous solution of hydroxypropylcellulose was sprayed and the mixture was dried to give a granulated powder. The granulated powder was milled by a milling machine (Power mill P-3, SHOWA KAGAKUKIKAI Co., LTD.) to give a milled powder. Croscarmellose sodium and magnesium stearate were added to the obtained milled powder and they were mixed in a blending machine (Tumbler 15 L, SHOWA KAGAKUKIKAI Co., LTD.) to give a mixed powder. The mixed powder was tableted by a rotary tableting machine (Correct 12HUK, Kikusui Seisakusho Ltd.) with a 13.0×7.0 mm punch to give core tablets (440 mg per tablet).

The core tablets were placed in a film coating machine (Doria coater DRC500, Powrex Corporation), a film coating solution with a composition ratio shown in Table 2-2 was sprayed to give film coated tablets (about 456.0 mg per tablet). The obtained film coated tablets were placed in a glass bottle, which was tightly sealed and preserved at 60° C. for 2 weeks.

TABLE 2-1

| additive | formulation amount (mg/tablet) |
| --- | --- |
| compound A | 80 |
| D-mannitol | 244 |
| crystalline cellulose | 80 |
| hydroxypropylcellulose | 12 |
| croscarmellose sodium | 20 |
| magnesium stearate | 4 |
| Total | 440 |

TABLE 2-2

| additive | formulation amount (mg/tablet) |
| --- | --- |
| hypromellose | 14.24 |
| titanium oxide | 1.60 |
| red ferric oxide | 0.16 |
| Total | 16.00 |

Reference Example 1

A core tablet containing compound A at a composition ratio shown in Table 3-1 was produced as follows.

That is, in a fluid bed granulator/dryer (FD-5S, Powrex Corporation), compound A, D-mannitol, and crystalline cellulose were preheated and mixed, an aqueous solution of hydroxypropylcellulose was sprayed and the mixture was dried to give a granulated powder. The granulated powder was milled by a milling machine (Power mill P-3, SHOWA KAGAKUKIKAI Co., LTD.) to give a milled powder. Crystalline cellulose, croscarmellose sodium and magnesium stearate were added to the obtained milled powder and they were mixed in a blending machine (Tumbler 15 L, SHOWA KAGAKUKIKAI Co., LTD.) to give a mixed powder. The mixed powder was tableted by a rotary tableting machine (Correct 12HUK, Kikusui Seisakusho Ltd.) with a 8.0 mmφ punch to give core tablets (220 mg per tablet).

The core tablets were placed in a film coating machine (Doria coater DRC500, Powrex Corporation), a film coating solution with a composition ratio shown in Table 3-2 was sprayed to give film coated tablets (about 228.0 mg per tablet).

TABLE 3-1

| additive | formulation amount (mg/tablet) |
| --- | --- |
| compound A | 40 |
| D-mannitol | 122 |
| crystalline cellulose | 40 |
| hydroxypropylcellulose | 6 |
| croscarmellose sodium | 10 |
| magnesium stearate | 2 |
| Total | 220 |

TABLE 3-2

| additive | formulation amount (mg/tablet) |
| --- | --- |
| hypromellose | 7.12 |
| titanium oxide | 0.80 |
| red ferric oxide | 0.02 |
| yellow ferric oxide | 0.06 |
| Total | 8.00 |

Example 1

A core tablet containing compound A at a composition ratio shown in Table 4-1 was produced as follows.

That is, in a fluid bed granulator/dryer (FD-5S, Powrex Corporation), compound A, D-mannitol, and crystalline cellulose were preheated and mixed, an aqueous solution of hydroxypropylcellulose was sprayed and the mixture was dried to give a granulated powder. The granulated powder was milled by a milling machine (Power mill P-3, SHOWA KAGAKUKIKAI Co., LTD.) to give a milled powder. Croscarmellose sodium and magnesium stearate were added to the obtained milled powder and they were mixed in a blending machine (Tumbler 15 L, SHOWA KAGAKUKIKAI Co., LTD.) to give a mixed powder. The mixed powder was tableted by a rotary tableting machine (Correct 12HUK, Kikusui Seisakusho Ltd.) with a 9.0 mmφ punch to give core tablets (280 mg per tablet).

The core tablets were placed in a film coating machine (Doria coater DRC500, Powrex Corporation), a film coating solution with a composition ratio shown in Table 4-2 was sprayed to give film coated tablets (about 290.2 mg per tablet). The obtained film coated tablets were placed in a glass bottle, which was tightly sealed and preserved at 60° C. for 2 weeks.

TABLE 4-1

| additive | formulation amount (mg/tablet) |
|---|---|
| compound A | 80 |
| D-mannitol | 126.2 |
| crystalline cellulose | 51 |
| hydroxypropylcellulose | 7.6 |
| croscarmellose sodium | 12.7 |
| magnesium stearate | 2.5 |
| Total | 280 |

TABLE 4-2

| additive | formulation amount (mg/tablet) |
|---|---|
| hypromellose | 9.06 |
| titanium oxide | 1.02 |
| red ferric oxide | 0.10 |
| Total | 10.2 |

Example 2

A core tablet containing compound A at a composition ratio shown in Table 5-1 was produced as follows.

That is, in a fluid bed granulator/dryer (FD-5S, Powrex Corporation), compound A, D-mannitol particles (PEARLITOL 100SD, ROQUETTE) and sodium starch glycolate were preheated and mixed, an aqueous solution of hydroxypropylcellulose was sprayed and the mixture was dried to give a granulated powder. The granulated powder was milled by a milling machine (Power mill P-3, SHOWA KAGAKUKIKAI Co., LTD.) to give a milled powder. Magnesium stearate was added to the obtained milled powder and they were mixed in a blending machine (Tumbler 15 L, SHOWA KAGAKUKIKAI Co., LTD.) to give a mixed powder. The mixed powder was tableted by a rotary tableting machine (Correct 12HUK, Kikusui Seisakusho Ltd.) with a 8.0 mmφ punch to give core tablets (200 mg per tablet).

The core tablets were placed in a film coating machine (Doria coater DRC500, Powrex Corporation), a film coating solution with a composition ratio shown in Table 5-2 was sprayed to give film coated tablets (about 208 mg per tablet). The obtained film coated tablets were placed in a glass bottle, which was tightly sealed and preserved at 60° C. for 2 weeks.

TABLE 5-1

| additive | formulation amount (mg/tablet) |
|---|---|
| compound A | 80 |
| D-mannitol particles | 102 |
| sodium starch glycolate | 10 |
| hydroxypropylcellulose | 6 |
| magnesium stearate | 2 |
| Total | 200 |

TABLE 5-2

| additive | formulation amount (mg/tablet) |
|---|---|
| hypromellose | 7.12 |
| titanium oxide | 0.80 |
| red ferric oxide | 0.08 |
| Total | 8.00 |

Example 3

A core tablet containing compound A at a composition ratio shown in Table 6-1 was produced as follows.

That is, in a fluid bed granulator/dryer (LAB-1, Powrex Corporation), compound A, D-mannitol particles (PEARLITOL 100SD, ROQUETTE), magnesium alumino metasilicate and sodium starch glycolate were preheated and mixed, an aqueous solution of hydroxypropylcellulose was sprayed and the mixture was dried to give a granulated powder. Magnesium stearate was added to the obtained granulated powder and they were mixed in a bag to give a mixed powder. The mixed powder was tableted by a rotary tableting machine (compact tableting machine, Kikusui Seisakusho Ltd.) with a 6.0 mmφ punch to give core tablets (110 mg per tablet).

The core tablets were placed in a film coating machine (Doria coater DRC500, Powrex Corporation), a film coating solution with a composition ratio shown in Table 6-2 was sprayed to give film coated tablets (about 114.0 mg per tablet). The obtained film coated tablets were placed in a glass bottle, which was tightly sealed and preserved at 60° C. for 2 weeks.

TABLE 6-1

| additive | formulation amount (mg/tablet) |
|---|---|
| compound A | 80 |
| D-mannitol particles | 18.8 |
| sodium starch glycolate | 5 |
| hydroxypropylcellulose | 3 |
| magnesium alumino metasilicate | 2.2 |
| magnesium stearate | 1 |
| Total | 110 |

TABLE 6-2

| additive | formulation amount (mg/tablet) |
|---|---|
| hypromellose | 3.56 |
| titanium oxide | 0.40 |
| red ferric oxide | 0.04 |
| Total | 4.00 |

Example 4

A core tablet containing compound A at a composition ratio shown in Table 7-1 was produced as follows.

That is, in a fluid bed granulator/dryer (MP-01, Powrex Corporation), compound A, D-mannitol, and crystalline cellulose were preheated and mixed, an aqueous solution of hydroxypropylcellulose was sprayed and the mixture was dried to give a granulated powder. Croscarmellose sodium and magnesium stearate were added to the obtained granulated powder, and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in Table 7-2 was sprayed to give film coated tablets (about 290 mg per tablet). The obtained film coated tablets were placed in a glass bottle, which was tightly sealed and preserved at 60° C. for 2 weeks.

TABLE 7-1

| additive | formulation amount (mg/tablet) |
| --- | --- |
| compound A | 80 |
| D-mannitol | 157.2 |
| crystalline cellulose | 20 |
| hydroxypropylcellulose | 7.6 |
| croscarmellose sodium | 12.7 |
| magnesium stearate | 2.5 |
| Total | 280 |

TABLE 7-2

| additive | formulation amount (mg/tablet) |
| --- | --- |
| hypromellose | 9.06 |
| titanium oxide | 1.02 |
| red ferric oxide | 0.026 |
| yellow ferric oxide | 0.077 |
| Total | 10.183 |

Example 5

A core tablet containing compound A at a composition ratio shown in Table 8 was produced as follows.

That is, in a fluid bed granulator/dryer (MP-01, Powrex Corporation), compound A, D-mannitol, and crystalline cellulose were preheated and mixed, an aqueous solution of hydroxypropylcellulose and polyethylene glycol 6000 was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in the aforementioned Table 7-2 was sprayed to give film coated tablets (about 290 mg per tablet). The obtained film coated tablets were placed in a glass bottle, which was tightly sealed and preserved at 60° C. for 2 weeks.

TABLE 8

| additive | formulation amount (mg/tablet) |
| --- | --- |
| compound A | 80 |
| D-mannitol | 156 |
| crystalline cellulose | 20 |
| hydroxypropylcellulose | 7.6 |
| polyethylene glycol 6000 | 1.2 |
| croscarmellose sodium | 12.7 |
| magnesium stearate | 2.5 |
| Total | 280 |

Example 6

A core tablet containing compound A at a composition ratio shown in Table 9 was produced as follows.

That is, in a fluid bed granulator/dryer (MP-01, Powrex Corporation), compound A, D-mannitol, and crystalline cellulose were preheated and mixed, a dispersion obtained by dispersing glycerol monostearate (hereinafter to be referred to as GMS) in aqueous hydroxypropylcellulose solution was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in the aforementioned Table 7-2 was sprayed to give film coated tablets (about 290 mg per tablet). The obtained film coated tablets were placed in a glass bottle, which was tightly sealed and preserved at 60° C. for 2 weeks.

TABLE 9

| additive | formulation amount (mg/tablet) |
| --- | --- |
| compound A | 80 |
| D-mannitol | 156 |
| crystalline cellulose | 20 |
| hydroxypropylcellulose | 7.6 |
| GMS | 1.2 |
| croscarmellose sodium | 12.7 |
| magnesium stearate | 2.5 |
| Total | 280 |

Example 7

A core tablet containing compound A at a composition ratio shown in Table 10 was produced as follows.

That is, in a fluid bed granulator/dryer (MP-01, Powrex Corporation), compound A, D-mannitol, and crystalline cellulose were preheated and mixed, an aqueous solution of hydroxypropylcellulose and polyethylene glycol 400 was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in the aforementioned Table 7-2 was sprayed to give film coated tablets (about 290 mg per tablet). The obtained film coated tablets were placed in a glass bottle, which was tightly sealed and preserved at 60° C. for 2 weeks.

TABLE 10

| additive | formulation amount (mg/tablet) |
|---|---|
| compound A | 80 |
| D-mannitol | 152.4 |
| crystalline cellulose | 20 |
| hydroxypropylcellulose | 7.6 |
| polyethylene glycol 400 | 4.8 |
| croscarmellose sodium | 12.7 |
| magnesium stearate | 2.5 |
| Total | 280 |

Example 8

A core tablet containing compound A at a composition ratio shown in Table 11 was produced as follows.

That is, in a fluid bed granulator/dryer (MP-01, Powrex Corporation), compound A, D-mannitol, and crystalline cellulose were preheated and mixed, an aqueous solution of hydroxypropylcellulose and triethyl citrate was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in the aforementioned Table 7-2 was sprayed to give film coated tablets (about 290 mg per tablet). The obtained film coated tablets were placed in a glass bottle, which was tightly sealed and preserved at 60° C. for 2 weeks.

TABLE 11

| additive | formulation amount (mg/tablet) |
|---|---|
| compound A | 80 |
| D-mannitol | 152.4 |
| crystalline cellulose | 20 |
| hydroxypropylcellulose | 7.6 |
| triethyl citrate | 4.8 |
| croscarmellose sodium | 12.7 |
| magnesium stearate | 2.5 |
| Total | 280 |

Example 9

A core tablet containing compound A at a composition ratio shown in Table 12 was produced as follows.

That is, in a fluid bed granulator/dryer (MP-01, Powrex Corporation), compound A, D-mannitol, and crystalline cellulose were preheated and mixed, a dispersion obtained by dispersing GMS in aqueous hydroxypropylcellulose solution was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in the aforementioned Table 7-2 was sprayed to give film coated tablets (about 290 mg per tablet). The obtained film coated tablets were placed in a glass bottle, which was tightly sealed and preserved at 60° C. for 2 weeks.

TABLE 12

| additive | formulation amount (mg/tablet) |
|---|---|
| compound A | 80 |
| D-mannitol | 147.2 |
| crystalline cellulose | 20 |
| hydroxypropylcellulose | 7.6 |
| GMS | 10 |
| croscarmellose sodium | 12.7 |
| magnesium stearate | 2.5 |
| Total | 280 |

Experimental Example 1

The film coated tablets obtained in Comparative Examples 1, 2, Examples 1-3, 5, 7-9 were examined for the amount of a decomposed product of compound A (U-2 (6-(4-aminophenyl)-1-(2,6-difluorobenzyl)-5-dimethylaminomethyl-3-(6-methoxypyridazin-3-yl)thieno[2,3-d]pyrimidine-2,4(1H,3H)-dione): relative retention time about 19 min) and the total amount of the decomposed product. The decomposed product was measured by extracting tablets with 0.05 mol/L sodium phosphate buffer (pH 2.0)/acetonitrile mixed solution (4:1) by the HPLC method. The test conditions of HPLC are shown below.

HPLC Test Conditions
detector: ultraviolet absorptiometer (measurement wavelength: 230 nm)
column: Intersil ODS-4, 3 μm, 4.6 mm i.d.×15 cm (GL Sciences Inc.)
column temperature: constant temperature near 40° C.
mobile phase A: 0.05 mol/L sodium phosphate buffer (pH 2.0)/acetonitrile mixed solution (4:1)
mobile phase B: acetonitrile/0.05 mol/L sodium phosphate buffer (pH 2.0) (3:2)
mobile phase feed: The mixing ratio of mobile phase A and mobile phase B was controlled as shown in Table 13.

TABLE 13

| time (min) | SOLUTION A (%) | SOLUTION B (%) |
|---|---|---|
| 0 (injecting) | 90 | 10 |
| 45 | 90 | 10 |
| 90 | 20 | 80 |
| 90.1 | 90 | 10 |
| 100 | 90 | 10 |

Time span of measurement: 90 min

Test Results 1

The film coated tablets of Comparative Examples 1, 2, Examples 1-3 were measured for a decomposed product before preservation and after preservation at 60° C. for 2 weeks, and the results of total decomposed product and U-2 are shown in Table 14.

TABLE 14

Test results of stability over days

| formulation | content percentage of compound A in core tablet | preservation | U-2 (%) | total decomposed product (%) |
|---|---|---|---|---|
| Comparative Example 1 | 4.5 | Initial | 0.06 | 0.23 |
|  |  | 60° C. 2 w | 0.37 | 0.97 |
| Comparative Example 2 | 18.2 | Initial | 0.09 | 0.41 |
|  |  | 60° C. 2 w | 0.26 | 0.81 |
| Example 1 | 28.6 | Initial | 0.10 | 0.40 |
|  |  | 60° C. 2 w | 0.22 | 0.65 |
| Example 2 | 40.0 | Initial | 0.09 | 0.38 |
|  |  | 60° C. 2 w | 0.16 | 0.56 |
| Example 3 | 72.7 | Initial | 0.04 | 0.26 |
|  |  | 60° C. 2 w | 0.11 | 0.49 |

The production of the total decomposed product and decomposed product U-2 was suppressed by increasing the content percentage of compound A in the tablets.

Test Results 2

The film coated tablet of Example 5 was measured for a decomposed product before preservation and after preservation at 60° C. for 2 weeks, and the results of total decomposed product and U-2 are shown in Table 15.

TABLE 15

Test results of stability over days

| formulation | preservation | U-2 (%) | total decomposed product (%) |
|---|---|---|---|
| Example 5 | Initial | 0.04 | 0.21 |
|  | 60° C. 2 w | 0.06 | 0.21 |

The production of the total decomposed product and decomposed product U-2 was suppressed by adding a fat and oil-like substance having a low melting point. Particularly, the production of decomposed product U-2, which increases markedly when a fat and oil-like substance having a low melting point is not added, was remarkably suppressed.

Test Results 3

The film coated tablets of Examples 7-9 were measured for a decomposed product before preservation and after preservation at 60° C. for 2 weeks, and the results of total decomposed product and U-2 are shown in Table 16.

TABLE 16

Test results of stability over days

| formulation | preservation | U-2 (%) | total decomposed product (%) |
|---|---|---|---|
| Example 7 | Initial | 0.04 | 0.22 |
|  | 60° C. 2 w | 0.06 | 0.23 |
| Example 8 | Initial | 0.04 | 0.27 |
|  | 60° C. 2 w | 0.06 | 0.28 |
| Example 9 | Initial | 0.04 | 0.23 |
|  | 60° C. 2 w | 0.06 | 0.20 |

The production of the total decomposed product and decomposed product U-2 was suppressed by adding a different fat and oil-like substance having a low melting point. Particularly, the production of decomposed product U-2, which increases markedly when a fat and oil-like substance having a low melting point is not added, was remarkably suppressed.

Examples 10-12

According to the formulation of Table 17, compound A, D-mannitol (PEARLITOL 50C, ROQUETTE), hydroxypropylcellulose, sodium starch glycolate and magnesium stearate were mixed in a bottle to give a mixed powder for tableting. The mixed powder was tableted by a tabletop tablet molding machine (HANDTAB200, ICHIHASHI SEIKI) with a 9.0 mmφ punch to give core tablets (300 mg per tablet). The obtained core tablets were placed in a glass bottle, which was tightly sealed and preserved at 60° C. for 2 weeks.

TABLE 17

| additive | formulation amount (mg/tablet) | | |
|---|---|---|---|
|  | Example 10 | Example 11 | Example 12 |
| compound A | 80 | 120 | 220 |
| D-mannitol | 193 | 153 | 53 |
| hydroxypropylcellulose | 9 | 9 | 9 |
| sodium starch glycolate | 15 | 15 | 15 |
| magnesium stearate | 3 | 3 | 3 |
| Total | 300 | 300 | 300 |

Experimental Example 2

The core tablets of Examples 10-12 were measured for a decomposed product before preservation and after preservation at 60° C. for 2 weeks, by the test method of Experimental Example 1, and the results of total decomposed product and U-2 are shown in Table 18.

TABLE 18

Test results of stability over days

| formulation | percent content of compound A in core tablet | preservation | U-2 (%) | total decomposed product (%) |
|---|---|---|---|---|
| Example 10 | 26.7 | Initial | 0.06 | 0.23 |
|  |  | 60° C. 2 w | 0.16 | 0.47 |
| Example 11 | 40.0 | Initial | 0.06 | 0.25 |
|  |  | 60° C. 2 w | 0.15 | 0.45 |
| Example 12 | 73.3 | Initial | 0.06 | 0.21 |
|  |  | 60° C. 2 w | 0.13 | 0.37 |

The production of the total decomposed product and decomposed product U-2 was suppressed by setting the percent content of compound A in the tablets to not less than 26.7%.

Reference Examples 2 and 3

According to the formulation of Table 19, compound A, D-mannitol (PEARLITOL 50C, ROQUETTE), hydroxypropylcellulose, sodium starch glycolate and magnesium stearate were mixed in a bottle to give a mixed powder for tableting. The mixed powder was tableted by a tabletop tablet molding machine (HANDTAB200, ICHIHASHI SEIKI) with a 9.0 mmφ punch.

TABLE 19

| additive | formulation amount (mg/tablet) | |
| --- | --- | --- |
| | Reference Example 2 | Reference Example 3 |
| compound A | 5 | 20 |
| D-mannitol | 268 | 253 |
| hydroxypropylcellulose | 9 | 9 |
| sodium starch glycolate | 15 | 15 |
| magnesium stearate | 3 | 3 |
| Total | 300 | 300 |

In Reference Examples 2 and 3 having a percent content of compound A of 1.7% and 6.7%, respectively, a tablet having a sufficient hardness as a preparation could not be obtained.

Comparative Example 3, Examples 13-15

According to the formulation of Table 20, compound A, D-mannitol particles (PEARLITOL 100SD, ROQUETTE), hydroxypropylcellulose, sodium starch glycolate and magnesium stearate were mixed in a bottle to give a mixed powder for tableting. The mixed powder was tableted by a tabletop tablet molding machine (HANDTAB200, ICHIHASHI SEIKI) with a 9.0 mmφ punch to give core tablets (300 mg per tablet). The obtained core tablets were placed in a glass bottle, which was tightly sealed and preserved at 60° C. for 2 weeks.

TABLE 20

| additive | formulation amount (mg/tablet) | | | |
| --- | --- | --- | --- | --- |
| | Comparative Example 3 | Example 13 | Example 14 | Example 15 |
| compound A | 5 | 80 | 120 | 220 |
| D-mannitol particles | 268 | 193 | 153 | 53 |
| hydroxypropylcellulose | 9 | 9 | 9 | 9 |
| sodium starch glycolate | 15 | 15 | 15 | 15 |
| magnesium stearate | 3 | 3 | 3 | 3 |
| Total | 300 | 300 | 300 | 300 |

Experimental Example 3

The core tablets of Comparative Example 3 and Examples 13-15 were measured for a decomposed product before preservation and after preservation at 60° C. for 2 weeks, by the test method of Experimental Example 1, and the results of total decomposed product and U-2 are shown in Table 21.

TABLE 21

Test results of stability over days

| formulation | percent content of compound A in core tablet | preservation | U-2 (%) | total decomposed product (%) |
| --- | --- | --- | --- | --- |
| Comparative Example 3 | 1.7 | Initial | 0.09 | 0.43 |
| | | 60° C. 2 w | 0.41 | 1.56 |
| Example 13 | 26.7 | Initial | 0.06 | 0.26 |
| | | 60° C. 2 w | 0.14 | 0.40 |
| Example 14 | 40.0 | Initial | 0.06 | 0.25 |
| | | 60° C. 2 w | 0.11 | 0.39 |
| Example 15 | 73.3 | Initial | 0.06 | 0.20 |
| | | 60° C. 2 w | 0.11 | 0.31 |

The production of the total decomposed product and decomposed product U-2 was suppressed by using D-mannitol particles (PEARLITOL 100SD, ROQUETTE) and setting the percent content of compound A in the tablet to not less than 26.7%.

Examples 16-18

The core tablets of Examples 16-18 containing compound A at composition ratios shown in Table 22 were produced as follows.

That is, compound A, D-mannitol particles, hydroxypropylcellulose, sodium starch glycolate and magnesium stearate were mixed in a bottle to give a mixed powder for tableting. The mixed powder was tableted by a tabletop tablet molding machine (HANDTAB200, ICHIHASHI SEIKI) with a 9.0 mmφ punch to give core tablets (300 mg per tablet). The obtained core tablets were placed in a glass bottle, which was tightly sealed and preserved at 60° C. for 2 weeks.

TABLE 22

| additive | formulation amount (mg/tablet) | | | | |
| --- | --- | --- | --- | --- | --- |
| | Example 10 | Example 13 | Example 16 | Example 17 | Example 18 |
| compound A | 80 | 80 | 80 | 80 | 80 |
| D-mannitol (PEARLITOL 50C; average diameter 30-60 μm) | 193 | — | — | — | — |
| D-mannitol particles (PEARLITOL 100SD; average particle size 75-150 μm) | — | 193 | — | — | — |
| D-mannitol particles (PEARLITOL 200SD; average particle size 100-200 μm) | — | — | 193 | — | — |
| D-mannitol particles (PEARLITOL 300DC; average particle size 270-370 μm) | — | — | — | 193 | — |
| D-mannitol particles (PEARLITOL 400DC; average particle size 350-450 μm) | — | — | — | — | 193 |
| hydroxypropylcellulose | 9 | 9 | 9 | 9 | 9 |
| sodium starch glycolate | 15 | 15 | 15 | 15 | 15 |
| magnesium stearate | 3 | 3 | 3 | 3 | 3 |
| Total | 300 | 300 | 300 | 300 | 300 |

Experimental Example 4

The core tablets of Examples 16-18 were measured for a decomposed product before preservation and after preservation at 60° C. for 2 weeks, by the test method of Experimental Example 1, and the results of total decomposed product and U-2 are shown in Table 23. The test results of the stability over days of the core tablets of the aforementioned Examples 10 and 13 are also shown in Table 23.

TABLE 23

Test results of stability over days

| formulation | percent content of compound A in core tablet | preservation | U-2 (%) | total decomposed product (%) |
|---|---|---|---|---|
| Example 10 | 26.7 | Initial | 0.06 | 0.23 |
|  |  | 60° C. 2 w | 0.16 | 0.47 |
| Example 13 | 26.7 | Initial | 0.06 | 0.26 |
|  |  | 60° C. 2 w | 0.14 | 0.40 |
| Example 16 | 26.7 | Initial | 0.06 | 0.24 |
|  |  | 60° C. 2 w | 0.14 | 0.41 |
| Example 17 | 26.7 | Initial | 0.06 | 0.26 |
|  |  | 60° C. 2 w | 0.20 | 0.57 |
| Example 18 | 26.7 | Initial | 0.06 | 0.28 |
|  |  | 60° C. 2 w | 0.18 | 0.53 |

When mannitol particles having various average particle sizes were used and the percent content of compound A in the tablet was set to 26.7%, the production of the total decomposed product and decomposed product U-2 was extremely suppressed when mannitol particles having an average particle size of 60-250 μm were used.

Examples 19-21

The core tablets of Examples 19-21 containing compound A at composition ratios shown in Table 24 were produced as follows.

That is, compound A, D-mannitol particles, hydroxypropylcellulose, sodium starch glycolate and magnesium stearate were mixed in a bottle to give a mixed powder for tableting. The mixed powder was tableted by a tabletop tablet molding machine (HANDTAB200, ICHIHASHI SEIKI) with a 9.0 mmφ punch to give core tablets (300 mg per tablet). The obtained core tablets were placed in a glass bottle, which was tightly sealed and preserved at 60° C. for 2 weeks.

TABLE 24

| additive | formulation amount (mg/tablet) | | | | |
|---|---|---|---|---|---|
|  | Example 11 | Example 14 | Example 19 | Example 20 | Example 21 |
| compound A | 120 | 120 | 120 | 120 | 120 |
| D-mannitol (PEARLITOL 50C) | 153 | — | — | — | — |
| D-mannitol particles (PEARLITOL 100SD) | — | 153 | — | — | — |
| D-mannitol particles (PEARLITOL 200SD) | — | — | 153 | — | — |
| D-mannitol particles (PEARLITOL 300DC) | — | — | — | 153 | — |
| D-mannitol particles (PEARLITOL 400DC) | — | — | — | — | 153 |
| hydroxypropylcellulose | 9 | 9 | 9 | 9 | 9 |
| sodium starch glycolate | 15 | 15 | 15 | 15 | 15 |
| magnesium stearate | 3 | 3 | 3 | 3 | 3 |
| Total | 300 | 300 | 300 | 300 | 300 |

Experimental Example 5

The core tablets of Examples 19-21 were measured for a decomposed product before preservation and after preservation at 60° C. for 2 weeks, and the results of total decomposed product and U-2 are shown in Table 25. The test results of the stability over days of the core tablets of the aforementioned Examples 11 and 14 are also shown in Table 25.

TABLE 25

Test results of stability over days

| formulation | percent content of compound A in core tablet | preservation | U-2 (%) | total decomposed product (%) |
|---|---|---|---|---|
| Example 11 | 40.0 | Initial | 0.06 | 0.25 |
|  |  | 60° C. 2 w | 0.15 | 0.45 |
| Example 14 | 40.0 | Initial | 0.06 | 0.25 |
|  |  | 60° C. 2 w | 0.11 | 0.39 |
| Example 19 | 40.0 | Initial | 0.06 | 0.26 |
|  |  | 60° C. 2 w | 0.13 | 0.40 |
| Example 20 | 40.0 | Initial | 0.07 | 0.41 |
|  |  | 60° C. 2 w | 0.19 | 0.61 |
| Example 21 | 40.0 | Initial | 0.07 | 0.41 |
|  |  | 60° C. 2 w | 0.16 | 0.56 |

When mannitol particles having various diameters were used and the percent content of compound A in the tablet was set to 40.0%, the production of the total decomposed product and decomposed product U-2 was extremely suppressed when mannitol particles having an average particle size of 60-250 μm were used.

Example 22

A core tablet containing compound A at a composition ratio shown in Table 26-1 was produced as follows.

That is, in a fluid bed granulator/dryer (FD-5S, Powrex Corporation), compound A, D-mannitol particles (PEARLITOL 100SD, ROQUETTE) and sodium starch glycolate were preheated and mixed, an aqueous solution of hydroxypropylcellulose was sprayed and the mixture was dried to give a granulated powder. The granulated powder was milled by a milling machine (Power mill P-3, SHOWA KAGAKUKIKAI Co., LTD.) to give a milled powder. Magnesium stearate was added to the obtained milled powder and they were mixed in a blending machine (Tumbler 15 L, SHOWA KAGAKUKIKAI Co., LTD.) to give a mixed powder. The mixed powder was tableted by a rotary tableting machine (compact tableting machine, Kikusui Seisakusho Ltd.) with a 6.0 mmφ punch to give core tablets (100 mg per tablet).

The core tablets were placed in a film coating machine (Doria coater DRC200, Powrex Corporation), a film coating solution with a composition ratio shown in Table 26-2 was sprayed to give film coated tablets (about 104.0 mg per tablet).

TABLE 26-1

| additive | formulation amount (mg/tablet) |
|---|---|
| compound A | 40 |
| D-mannitol particles | 51 |
| sodium starch glycolate | 5 |
| hydroxypropylcellulose | 3 |
| magnesium stearate | 1 |
| Total | 100 |

TABLE 26-2

| additive | formulation amount (mg/tablet) |
|---|---|
| hypromellose | 3.56 |
| titanium oxide | 0.4 |
| red ferric oxide | 0.04 |
| Total | 4.00 |

Example 23

A core tablet containing compound A at a composition ratio shown in Table 27 is produced as follows.

That is, in a fluid bed granulator/dryer (FD-5S, Powrex Corporation), compound A, D-mannitol particles (PEARLITOL 100SD, ROQUETTE), and sodium starch glycolate are preheated and mixed, an aqueous solution of hydroxypropylcellulose is sprayed and the mixture is dried to give a granulated powder. The granulated powder is milled by a milling machine (Power mill P-3, SHOWA KAGAKUKIKAI Co., LTD.) to give a milled powder. Magnesium stearate is added to the obtained milled powder and they are mixed in a blending machine (Tumbler 15 L, SHOWA KAGAKUKIKAI Co., LTD.) to give a mixed powder. The mixed powder is tableted by a rotary tableting machine (compact tableting machine, Kikusui Seisakusho Ltd.) with a 7.0 mmφ punch to give core tablets (125 mg per tablet).

TABLE 27

| additive | formulation amount (mg/tablet) |
|---|---|
| compound A | 50 |
| D-mannitol particles | 63.75 |
| sodium starch glycolate | 6.25 |
| hydroxypropylcellulose | 3.75 |
| magnesium stearate | 1.25 |
| Total | 125 |

Examples 24-29

The core tablets of Examples 24-29 containing compound A at composition ratios shown in Tables 28-1 and 28-2 were produced as follows.

That is, in a fluid bed granulator/dryer (MP-01, Powrex Corporation), compound A, D-mannitol, and crystalline cellulose were preheated and mixed, an aqueous solution of hydroxypropylcellulose and polyethylene glycol 6000 was sprayed and the mixture was dried to give a granulated powder. Croscarmellose sodium and magnesium stearate were added to the obtained granulated powder and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet).

The core tablets were placed in a film coating machine (Freund Corporation, HC-LABO-20), a film coating solution with a composition ratio shown in the aforementioned Table 7-2 was sprayed to give film coated tablets of Examples 24-29 (about 290 mg per tablet). The obtained film coated tablets were placed in a glass bottle, which was tightly sealed and preserved at 60° C. for 2 weeks.

TABLE 28-1

| | formulation amount (mg/tablet) | | | |
|---|---|---|---|---|
| additive | Example 4 | Example 24 | Example 25 | Example 5 |
| compound A | 80 | 80 | 80 | 80 |
| D-mannitol | 157.2 | 156.9 | 156.6 | 156 |
| crystalline cellulose | 20 | 20 | 20 | 20 |
| hydroxypropylcellulose | 7.6 | 7.6 | 7.6 | 7.6 |
| polyethylene glycol 6000 | 0 | 0.3 | 0.6 | 1.2 |
| croscarmellose sodium | 12.7 | 12.7 | 12.7 | 12.7 |
| magnesium stearate | 2.5 | 2.5 | 2.5 | 2.5 |
| Total | 280 | 280 | 280 | 280 |

TABLE 28-2

| | formulation amount (mg/tablet) | | | |
|---|---|---|---|---|
| additive | Example 26 | Example 27 | Example 28 | Example 29 |
| compound A | 80 | 80 | 80 | 80 |
| D-mannitol | 154.4 | 152.4 | 148.8 | 143.2 |
| crystalline cellulose | 20 | 20 | 20 | 20 |
| hydroxypropylcellulose | 7.6 | 7.6 | 7.6 | 7.6 |
| polyethylene glycol 6000 | 2.8 | 4.8 | 8.4 | 14.0 |
| croscarmellose sodium | 12.7 | 12.7 | 12.7 | 12.7 |
| magnesium stearate | 2.5 | 2.5 | 2.5 | 2.5 |
| Total | 280 | 280 | 280 | 280 |

Experimental Example 6

The film coated tablets of Examples 24-29 were measured for a decomposed product before preservation and after preservation at 60° C. for 2 weeks, by the test method described in Experimental Example 1, and the results of total decomposed product and U-2 are shown in Table 29. In addition, the aforementioned film coated tablet of Example 4 was measured for a decomposed product before preservation and after preservation at 60° C. for 2 weeks, by a similar method, and the results of total decomposed product and U-2 are shown in Table 29. The test results of the stability over days of the film-coated tablet of the aforementioned Example 5 are also shown in Table 29.

TABLE 29

Test results of stability over days

| Example (content (wt %) of PEG in core tablet) | preservation | U-2 (%) | total decomposed product (%) |
|---|---|---|---|
| Example 4 (0%) | Initial | 0.04 | 0.23 |
| | 60° C. 2 w | 0.16 | 0.43 |
| Example 24 (0.1 wt %) | Initial | 0.04 | 0.24 |
| | 60° C. 2 w | 0.12 | 0.33 |
| Example 25 (0.2 wt %) | Initial | 0.04 | 0.25 |
| | 60° C. 2 w | 0.08 | 0.27 |
| Example 5 (0.4 wt %) | Initial | 0.04 | 0.21 |
| | 60° C. 2 w | 0.06 | 0.21 |
| Example 26 (1 wt %) | Initial | 0.07 | 0.26 |
| | 60° C. 2 w | 0.11 | 0.32 |
| Example 27 (1.7 wt %) | Initial | 0.04 | 0.27 |
| | 60° C. 2 w | 0.06 | 0.33 |
| Example 28 (3 wt %) | Initial | 0.07 | 0.31 |
| | 60° C. 2 w | 0.12 | 0.39 |
| Example 29 (5 wt %) | Initial | 0.07 | 0.35 |
| | 60° C. 2 w | 0.15 | 0.54 |

The production of the total decomposed product and decomposed product U-2 was markedly suppressed in a tablet setting a percent content of PEG, which is a fat and oil-like substance having a low melting point, (particularly, PEG 6000) to 0.2-1.7 wt % (preferably 0.2-0.4 wt %) relative to the core tablet.

Reference Example 4, Examples 30-34

Core tablets containing compound A at composition ratios shown in Tables 30-1 and 30-2 were produced as follows.

That is, in a fluid bed granulator/dryer (MP-01, Powrex Corporation), compound A, D-mannitol, and crystalline cellulose were preheated and mixed, an aqueous solution of hydroxypropylcellulose was sprayed and dried to give a granulated powder. Croscarmellose sodium, magnesium stearate and, in Examples 30-34, polyethylene glycol having various average molecular weights (specifically, polyethylene glycol 6000 (average molecular weight: 7300-9300), POLYOX WSR N-10 (average molecular weight: 100000), POLYOX WSR N-205 (average molecular weight: 600000), POLYOX WSR N-12K (average molecular weight: 1000000), POLYOX WSR 303 (average molecular weight: 7000000)) were added to the obtained granulated powder, and they were mixed in a bag to give a mixed powder. The mixed powder was tableted by a rotary tableting machine (Kikusui Seisakusho Ltd., compact tableting machine) with a 9 mmφ punch to give core tablets (280 mg per tablet, Reference Example 4) and (284.8 mg, Examples 30-34).

The obtained core tablets were placed in a glass bottle, which was tightly sealed and preserved at 60° C. for 2 weeks.

TABLE 30-1

| additive | formulation amount (mg/tablet) | | |
|---|---|---|---|
| | Reference Example 4 | Example 30 | Example 31 |
| compound A | 80 | 80 | 80 |
| D-mannitol | 157.2 | 157.2 | 157.2 |
| crystalline cellulose | 20 | 20 | 20 |
| hydroxypropylcellulose | 7.6 | 7.6 | 7.6 |
| croscarmellose sodium | 12.7 | 12.7 | 12.7 |
| polyethylene glycol 6000 | — | 4.8 | — |
| POLYOX WSR N-10 | — | — | 4.8 |
| POLYOX WSR N-205 | — | — | — |
| POLYOX WSR N-12K | — | — | — |
| POLYOX WSR 303 | — | — | — |
| magnesium stearate | 2.5 | 2.5 | 2.5 |
| Total | 280 | 284.8 | 284.8 |

TABLE 30-2

| additive | formulation amount (mg/tablet) | | |
|---|---|---|---|
| | Example 32 | Example 33 | Example 34 |
| compound A | 80 | 80 | 80 |
| D-mannitol | 157.2 | 157.2 | 157.2 |
| crystalline cellulose | 20 | 20 | 20 |
| hydroxypropylcellulose | 7.6 | 7.6 | 7.6 |
| croscarmellose sodium | 12.7 | 12.7 | 12.7 |
| polyethylene glycol 6000 | — | — | — |
| POLYOX WSR N-10 | — | — | — |
| POLYOX WSR N-205 | 4.8 | — | — |
| POLYOX WSR N-12K | — | 4.8 | — |
| POLYOX WSR 303 | — | — | 4.8 |
| magnesium stearate | 2.5 | 2.5 | 2.5 |
| Total | 284.8 | 284.8 | 284.8 |

Experimental Example 7

The core tablets obtained in Tables 30-1 and 30-2 were measured for a decomposed product before preservation and after preservation at 60° C. for 2 weeks, and the results of total decomposed product and U-2 are shown in Table 31.

TABLE 31

Test results of stability over days

| Example | preservation | U-2 (%) | total decomposed product (%) |
|---|---|---|---|
| Reference Example 4 (tablet not containing PEG) | Initial | 0.06 | 0.24 |
| | 60° C. 2 w | 0.20 | 0.50 |
| Example 30 (average molecular weight of PEG: 7300-9300) | Initial | 0.05 | 0.26 |
| | 60° C. 2 w | 0.09 | 0.37 |
| Example 31 (average molecular weight of PEG: 100000) | Initial | 0.05 | 0.24 |
| | 60° C. 2 w | 0.12 | 0.31 |
| Example 32 (average molecular weight of PEG: 600000) | Initial | 0.05 | 0.19 |
| | 60° C. 2 w | 0.17 | 0.40 |
| Example 33 (average molecular weight of PEG: 1000000) | Initial | 0.05 | 0.19 |
| | 60° C. 2 w | 0.17 | 0.40 |
| Example 34 (average molecular weight of PEG: 700000) | Initial | 0.05 | 0.18 |
| | 60° C. 2 w | 0.17 | 0.41 |

In a tablet containing PEG, the production of the total decomposed product and decomposed product U-2, each derived from compound A, was suppressed. In particular, in a tablet containing PEG having an average molecular weight of 7300-9300, or 100000, the production of the total decomposed product and decomposed product U-2 was markedly suppressed.

Example 35

A core tablet containing compound A at a composition ratio shown in Table 32-1 was produced as follows.

That is, in a fluid bed granulator/dryer (FD-5S, Powrex Corporation), compound A, D-mannitol, and crystalline cellulose were preheated and mixed, an aqueous solution of hydroxypropylcellulose and polyethylene glycol 6000 was sprayed and the mixture was dried to give a granulated powder. The granulated powder was milled by a milling machine (Power mill P-3, SHOWA KAGAKUKIKAI Co., LTD.) to give a milled powder. Croscarmellose sodium and magnesium stearate were added to the obtained milled powder and they were mixed in a blending machine (Tumbler 15 L, SHOWA KAGAKUKIKAI Co., LTD.) to give a mixed powder. The mixed powder was tableted by a rotary tableting machine (AQUARIUS, Kikusui Seisakusho Ltd.) with a 12.0λ8.4 mmφ punch to give core tablets (420 mg per tablet).

The core tablet was placed in a film coating machine (Doria coater DRC500, Powrex Corporation), a film coating solution with a composition ratio shown in Table 32-2 was sprayed and the tablet was coated with a trace amount of Carnauba wax (0.012 mg per tablet) to give a film coated tablet (about 435 mg per tablet). The obtained film-coated tablets were placed in a glass bottle, which was tightly sealed and preserved at 60° C. for 2 weeks.

TABLE 32-1

| additive | formulation amount (mg/tablet) |
|---|---|
| compound A | 120 |
| D-mannitol | 234 |
| crystalline cellulose | 30 |
| hydroxypropylcellulose | 11.4 |
| polyethylene glycol 6000 | 1.8 |
| croscarmellose sodium | 19.05 |
| magnesium stearate | 3.75 |
| Total | 420 |

TABLE 32-2

| additive | formulation amount (mg/tablet) |
|---|---|
| hypromellose | 13.5 |
| titanium oxide | 1.5 |
| red ferric oxide | 0.15 |
| Total | 15.15 |

Experimental Example 8

The film coated tablet of Example 35 was measured for a decomposed product before preservation and after preservation at 60° C. for 2 weeks, and the results of total decomposed product and U-2 are shown in Table 33.

TABLE 33

Test results of stability over days

| formulation | preservation | U-2 (%) | total decomposed product (%) |
|---|---|---|---|
| Example 35 | Initial | 0.06 | 0.25 |
| | 60° C. 2 w | 0.07 | 0.23 |

From the results of this test, it was clarified that, even when the total amount of the core tablet is 420 mg, the production of the total decomposed product and decomposed product U-2 was suppressed by adding a fat and oil-like substance having a low melting point (particularly, polyethylene glycol) to the core tablet.

This application is based on patent application No. 2015-037462 filed in Japan, the contents of which are encompassed in full herein.

The invention claimed is:

1. A tablet comprising N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof in an amount of 40 mg measured based on free form N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, 51 mg of D-mannitol particles having an average particle size of 70-200 μm, 5 mg of sodium starch glycolate, 3 mg of hydroxypropylcellulose, and 1 mg of magnesium stearate.

2. The tablet according to claim 1, further comprising a film-coating, wherein the film-coating comprises hydroxypropylmethylcellulose, titanium oxide, and red ferric oxide.

3. The tablet according to claim 1, further comprising a film-coating, wherein the film-coating comprises 3.56 mg of hydroxypropylmethylcellulose, 0.40 mg of titanium oxide, and 0.04 mg of red ferric oxide.

4. The tablet of claim 1, wherein the D-mannitol particles have an average particle size of 75-150 μm.

5. A tablet comprising N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof in an amount of 120 mg measured based on free form N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, 153 mg of D-mannitol particles having an average particle size of 70-200 μm, 15 mg of sodium starch glycolate, 9 mg of hydroxypropylcellulose, and 3 mg of magnesium stearate.

6. The tablet according to claim 5, further comprising a film-coating, wherein the film-coating comprises hydroxypropylmethylcellulose, titanium oxide, and red ferric oxide.

7. The tablet of claim 5, wherein the D-mannitol particles have an average particle size of 75-150 μm.

8. A tablet comprising N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof in an amount of 80 mg measured based on free form N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, 102 mg of D-mannitol particles having an average particle size of 70-200 μm, 10 mg of sodium starch glycolate, 6 mg of hydroxypropylcellulose, and 2 mg of magnesium stearate.

9. The tablet according to claim 8, further comprising a film-coating, wherein the film-coating comprises hydroxypropylmethylcellulose, titanium oxide, and red ferric oxide.

10. The tablet according to claim 8, further comprising a film-coating, wherein the film-coating comprises 7.12 mg of hydroxypropylmethylcellulose, 0.80 mg of titanium oxide, and 0.08 mg of red ferric oxide.

11. The tablet of claim 8, wherein the D-mannitol particles have an average particle size of 75-150 μm.

12. A method of making a tablet of claim 1, said method comprising:
1) mixing N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof with D-mannitol particles having an average particle size of 70-200 μm and sodium starch glycolate;
2) spraying into a mixture of step 1) a solution of hydroxypropylcellulose in a solvent or dispersing medium;
3) drying or sieving a mixture of step 2) to afford a granulated powder or a sieved powder;
4) adding magnesium stearate to the granulated powder or sieved powder of step 3) and mixing to afford granules for tableting;
5) tableting the granules of step 4) to afford a core tablet; and, optionally, 6) spraying a film-coating solution onto the core tablet of step 5) to afford a film-coated tablet.

13. A method of making a tablet of claim 5, said method comprising:
1) mixing N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof with D-mannitol particles having an average particle size of 70-200 μm and sodium starch glycolate;
2) spraying into a mixture of step 1) a solution of hydroxypropylcellulose in a solvent or dispersing medium;
3) drying or sieving a mixture of step 2) to afford a granulated powder or a sieved powder;
4) adding magnesium stearate to the granulated powder or sieved powder of step 3) and mixing to afford granules for tableting;
5) tableting the granules of step 4) to afford a core tablet; and, optionally,
6) spraying a film-coating solution onto the core tablet of step 5) to afford a film-coated tablet.

14. A method of making a tablet of claim 8, said method comprising:
1) mixing N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a salt thereof with D-mannitol particles having an average particle size of 70-200 μm and sodium starch glycolate;
2) spraying into a mixture of step 1) a solution of hydroxypropylcellulose in a solvent or dispersing medium;
3) drying or sieving a mixture of step 2) to afford a granulated powder or a sieved powder;
4) adding magnesium stearate to the granulated powder or sieved powder of step 3) and mixing to afford granules for tableting;
5) tableting the granules of step 4) to afford a core tablet; and, optionally,
6) spraying a film-coating solution onto the core tablet of step 5) to afford a film-coated tablet.

* * * * *